United States Patent [19]
Darby

[11] Patent Number: 5,138,777
[45] Date of Patent: Aug. 18, 1992

[54] POST-OPERATIVE SHOES FOR USE AFTER FOREFOOT SURGERY

[75] Inventor: H. Darrel Darby, Huntington, W. Va.

[73] Assignee: Darco International, Inc., Huntington, W. Va.

[21] Appl. No.: 611,588

[22] Filed: Nov. 13, 1990

[51] Int. Cl.[5] ............................. A43B 7/00; A43B 7/14
[52] U.S. Cl. ............................................ 36/88; 36/110
[58] Field of Search ..................................... 36/88, 110

[56] References Cited
U.S. PATENT DOCUMENTS

| 4,425,721 | 1/1984 | Spronken | 36/88 |
| 4,546,557 | 10/1985 | Barouk et al. | 36/110 |
| 4,677,767 | 7/1987 | Darby | 36/110 |
| 4,726,127 | 2/1988 | Barouk | 36/110 |
| 4,821,432 | 4/1989 | Reiber | 36/110 |

OTHER PUBLICATIONS

Article by S. Barouk, pp. 197–201 of publication Le Chaussage by J. Claustre and L. Simon, published by Masson, Paris, France 1988 and translation.

*Primary Examiner*—Paul T. Sewell
*Assistant Examiner*—M. Denise Patterson
*Attorney, Agent, or Firm*—Sughrue, Mion, Zinn, Macpeak & Seas

[57] ABSTRACT

A wedge undersole of triangular shaped configuration as viewed from a side thereof is integrated to a mid-sole of a sole assembly formed of an impact-absorbing material and having a thickness which varies over the length of the shoe, having flat top and bottom surfaces, and having its greatest thickness at the heel of the shoe and tapering in the direction of the open toe region formed by a upper assembly secured to the sole assembly. The upper assembly is adapted to surround the heel sides and dorsal portion of the foot. Preferably, the upper assembly has a heel region extending upwardly from the sole assembly and forward portions divided into left and right flaps adapted to cover the dorsal region of the foot and strap interconnecting outer face portions of the left an right flaps. The wedge undersole ensures that the top surface of the mid-sole extends upwardly and forwardly in the direction of the open toe region of the shoe with the front surface of the wedge undersole terminating proximate to the metatarsal heads of the foot. The weight of and pressure on the forefoot is fully relieved while the portion of the mid-sole from the terminating of the wedge undersole proximate to the metatarsal heads acts to fully support the forefoot at an upwardly oblique angle. That portion of the mid-sole also underlies the forefoot to completely protect the forefoot from impact along both sides thereof at the open toe region of the shoe, and at the front of the mid-sole.

8 Claims, 2 Drawing Sheets

POST-OPERATIVE SHOES FOR USE AFTER FOREFOOT SURGERY

FIELD OF THE INVENTION

The present invention is directed to post-operative surgical shoes and, more particularly, to such shoes which are highly useful after forefoot surgery, trauma to the forefoot or for healing of planter ulcerations or other lesions, and to such shoes which effectively and nearly completely remove the pressure from the forefoot.

BACKGROUND OF THE INVENTION

Following many surgical procedures to the forefoot and, in many instances, where no surgical procedures have been done, it is extremely beneficial to completely remove the pressure from the forefoot. Such pressure removal is highly desirable after forefoot surgery such as following hammertoe procedures when pins have been implanted through the toes and cross the M-P joints; after mid-tarsal amputation; or after hallux valgus procedures. Additionally, where the patient is suffering trauma to the forefoot as when diabetic ulcerations are present beneath the M-P joints or toes, similarly, when lesions of any type are present on the forefoot or toes; when it is necessary to treat the insensitive foot; and where ischemic changes including gangrene are present and involve the toes or forefoot, it is highly desirable to remove weight from the forefoot.

In the past, attempts have been made to protect the forefoot following surgery. A post-operative shoe sold under the registered trademark IPOS ® by Ipos USA, 2045 Niagara Falls Boulevard. Niagara Falls, N.Y., is so designed as to elevate the foot at an approximately 10° angle to remove pressure from the forefoot. In order to allow the patient to have an even gait in the IPOS ® shoe, however, the doctor is required to build up the sole of the shoe on the unaffected foot of the patient. The IPOS ® post-operative shoe terminates at the mid-metatarsal, leaving the affected forefoot area totally unprotected. Further, the patient is uncomfortable during walking due to the pressure where the shoe ends under the mid-foot.

U.S. Pat. No. 4,821,432 disclosing a walking adaptor that attaches itself to the sole of a post-operative shoe to promote easier ambulation. The adaptor is of semi-cylindrical form having a flat surface bearing a pressure sensitive adhesive permitting the sector-shaped adaptor to be press fitted to the bottom of the sole of the post-operative shoe at approximately a mid-position between the tip and heel of the shoe. While the attachable rocker functions to facilitate ambulation, it does not adequately elevate the forefoot or remove weight from the forefoot.

It is therefore a primary object of the present invention to provide an improved surgical shoe which functions to completely remove the pressure from the forefoot which effectively removes the weight from the forefoot, which fully protects and supports the forefoot during the duration of the healing process, and which renders the shoe comfortable during ambulation of the patient wearing the shoe by providing to the patient, equal heel strike on both feet, and equal toe off.

SUMMARY OF THE INVENTION

This invention is directed to a post-operative shoe for use particularly in elevating and supporting a post-operative or otherwise traumatized forefoot of a patient's foot comprising an upper assembly secured to a sole assembly. The upper assembly is adapted to surround the heel, sides and dorsal portions of the foot and includes an open toe region, a heel region upwardly from the sole assembly and forward portions divided into left and right flaps adapted to cover the dorsal region of the foot. Strap means are provided for interconnecting outer face portions of the left and right flaps. Such sole assembly is formed partially of an inner sole conforming generally to the plantar aspect of the foot and a mid-sole of an impact-absorbing material underlying the inner sole and having top and bottom surfaces. The mid-sole varies in thickness over the length of the shoe having its greater thickness at the heel and tapering in the direction of the shoe tip.

The improvement comprises a wedge undersole of triangular shape configuration when viewed from a side, integrated to the mid-sole on the bottom surface thereof in proximity to the heel of the shoe and tapering from a front end thereof to a rear edge and being of a thickness such that the top surface of the mid-sole extends obliquely upwardly in the direction of the tip of the shoe. The wedge undersole terminates at a front end remote from the shoe heel proximate to the metatarsal heads of the foot such that the weight of and the pressure on the forefoot is fully relieved while the portion of the mid-sole, from the termination of the wedge undersole at said mid-metatarsal, acts to fully support said forefoot at said upwardly oblique angle while underlying the forefoot to protect the forefoot from both side and frontal impact.

The wedge undersole may be integrally molded with the mid-sole, or an attached separate element, preferably via a layer of adhesive interposed between the upper surface of the wedge undersole and the bottom surface of the mid-sole.

Preferably, the mid-sole is provided with a rearwardly and upwardly oblique surface from the heel of the sole assembly in a direction towards the tip of the shoe which is downwardly oblique and which terminates at the junction of the tapered edge of the wedge undersole at the mid-sole to permit rear rocking of the post-operative she during ambulation by the patient.

Preferably, the wedge undersole terminates in a front face which is vertical with respect to the bottom surface of the triangular shaped wedge undersole. The wedge undersole, at least in the area of said vertical front face, may be formed of a solid TPR to rigidify the sole assembly in the vicinity of the mid-metatarsal region of the foot to facilitate forward rocking of the sole assembly about a pivot point defined by the intersection of the bottom surface and front surface of the wedge undersole. The bottom front edge of the wedge undersole may be curved to facilitate such forward rocking of the post-operative shoe sole assembly during ambulation of the patient.

DESCRIPTION OF THE PREFERRED EMBODIMENT

Figure 2:
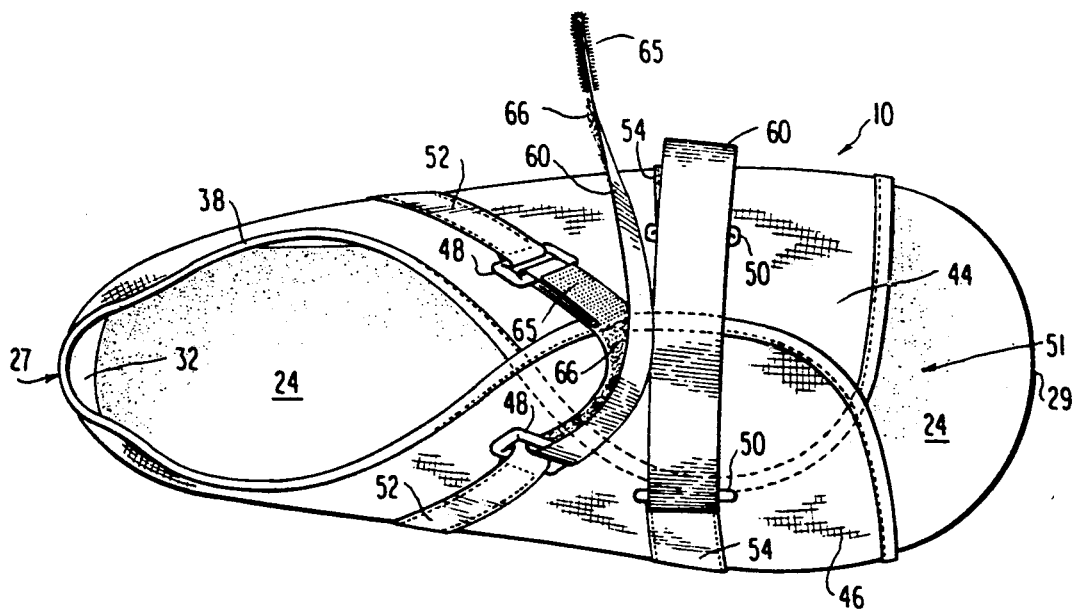
FIG. 2 is a top plan view of the post-operative shoe of FIG. 1.
Figure 3:
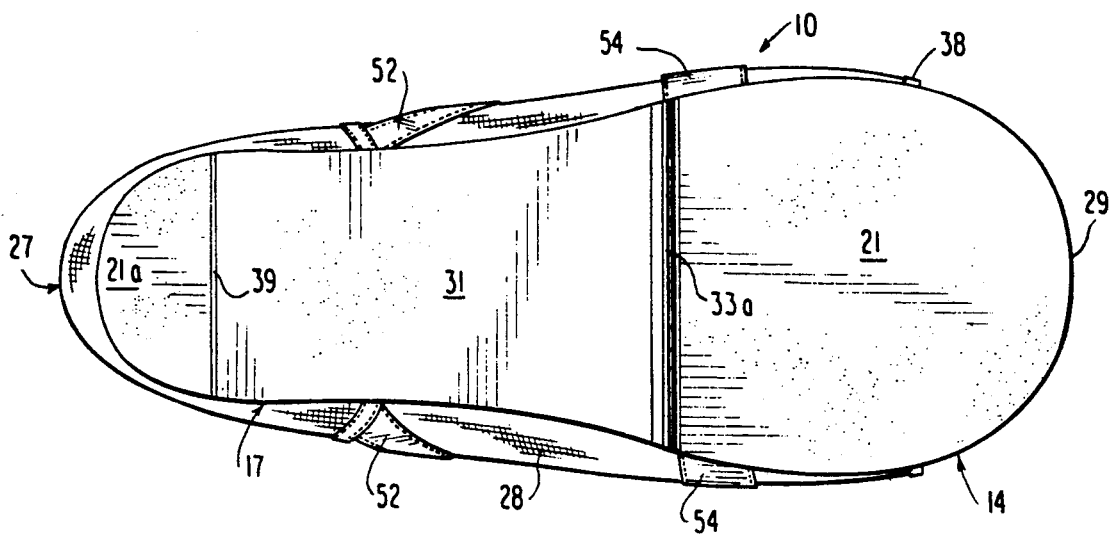
FIG. 3 is a bottom plan view of the post-operative shoe of FIGS. 1 and 2.

The surgical shoe of the present invention is constructed in part in accordance with the shock absorbing surgical shoe of my earlier issued U.S. Pat. No. 4,677,767, issued Jul. 7, 1987 and entitled Shock Absorbing Surgical Shoe. In that respect, referring to the drawings which illustrate a preferred embodiment of the invention, the post-operative shoe is indicated generally at 10, with an upper assembly or upper, designated generally by the numeral 12, which upper is quite similar to that of my earlier patent. The difference resides essentially in the sole assembly indicated generally at 14 which consists of an inner sole 24, a mid-sole 16 and a lift wedge undersole 17 fixedly mounted thereto. The undersole 17 may be, alternatively, integrally formed with the mid-sole 16. The upper assembly 12 is secured to the mid-sole 16, which is planar, by adhesive bonding with a layer of adhesive 19, applied to the upper surface 18 of the mid-sole and inner sole 24 of a foam plastic material capable of molding or conforming to the Plantar surface of the foot, then bonded by adhesive 19 to the top of mid-sole 16. The mid-sole 16 may be formed of a resilient, flexible material, preferably ethylene-vinyl acetate copolymer. With the lift wedge undersole 17 formed separately from mid-sole 16, the lower surface 21 of the mid-sole 16 is bonded to the upper surface 23 of the undersole 17 by an adhesive bonding layer 25. The sole assembly 14, including mid-sole 16, undersole 17 and the soft insole 24, as may be seen from FIGS. 2 and 3, is symmetrical with respect to the vertical plane passing through the longitudinal axis thereof.

The upper assembly 12, known conventionally as the "upper", is secured to the mid-sole 16 by conventional techniques, preferably by adhesive bonding using adhesive bonding layer 19. The upper assembly 12 has an outer wall 28 of a substantially elastic, flexible material such as nylon mesh. As an example, a lining of a soft conformable material, for example, a plastic foam 32, is laminated and being bonded to the interface of the outer wall 28. The upper assembly 12 extends from the heel indicated generally at 27 along the sides of the shoe in the direction of the shoe tip 29. The upper has an open toe region, indicated generally at 51. A trim strip 38 is secured as by sewing along the edges of the upper.

Figure 1:
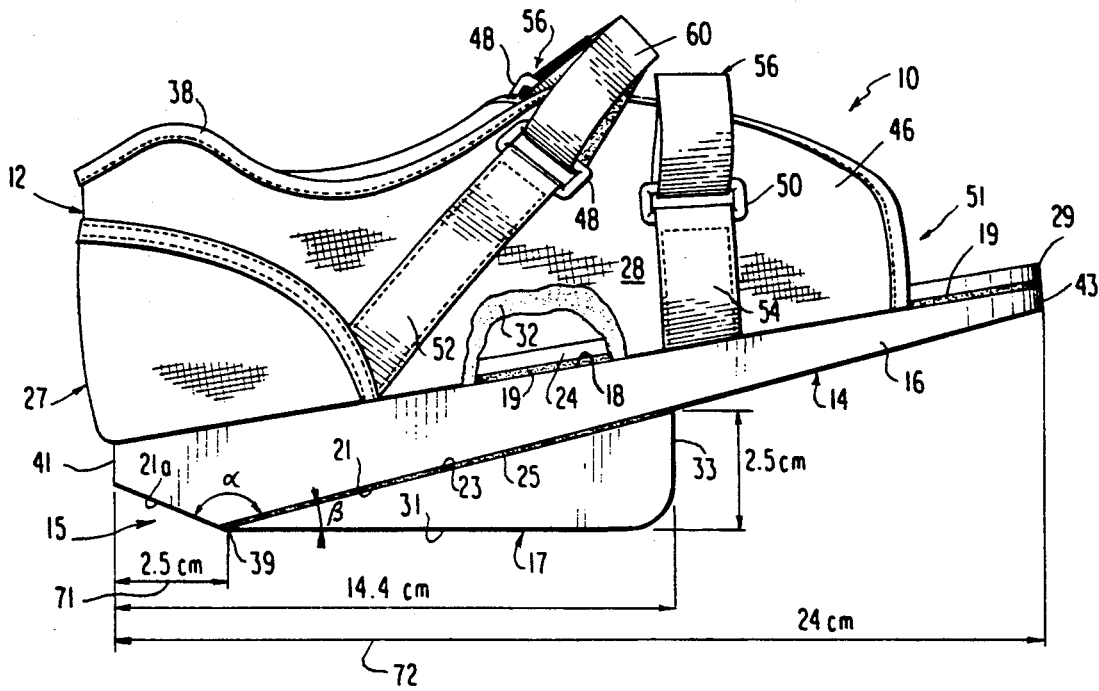
FIG. 1 is a side elevational view of the improved surgical post-operative shoe useful after forefoot surgery, trauma to the forefoot and for healing of Plantar ulcerations or other lesions, or to facilitate general medical treatment of the forefoot, forming a preferred embodiment of the invention.

The forward portion of the upper assembly is formed with left and right flaps 44, 46, respectively. The left flap 46 is longer than the right and folded under as seen in FIGS. 1, 2. In conformance with U.S. Pat. No. 4,677,767, the outer face of each of the flaps are provided with two elongated rings 48, 50. The rings 48, 50 are retained by straps 52, 54 of flexible but non-elastic material. The rear strap is angled downwardly and rearwardly and the forward one at right angles to the plane of the upper surface 18 of mid-sole 16. The forward strap is shorter than the rear. The forward and rearward rings, respectively, on the two flaps are aligned transversely with one another. A closure strap 56 is provided for each pair of rings. Each closure strap consists of a cloth tape having a first end portion 60 extending approximately ¼ of the length of the strap and being covered on each face with a fabric layer having projecting hook-like elements 65, while one face of the remainder of the closure strap is covered with loop like elements. The hook and loop elements engage and such elements are of the type sold under the registered trademark VELCRO®, for example.

The closure strap is threaded through one of the elongated rings, for example, ring 48 on one flap of the shoe within the end portion 60 located below the ring and the loop-like element face directed outwardly. The strap is passed through the ring to the juncture of the end portion 60 and the remainder of the strap. At this point, the end portion 60 is folded over so that the hook-like element layer 62 engages the loop-like elements of the adjacent portion of the strap, thereby restraining the strap on the corresponding ring. In order to close the shoe on an inserted foot, the free end of the strap is passed through the corresponding ring on the opposite flap, and doubled back to place the free end and engage it with the fastening element layer 64.

It is to be noted in the instant post-operative shoe that the heel region 27 of the shoe upper is approximately at right angles to the plane of the upper surface 18 of mid-sole 16.

The present invention is directed to a modification of the shoe structure as exemplified by U.S. Pat. No. 4,677,767 in an effort to solve a problem which became apparent to the applicant recently. The modification permits the post-operative shoe to function to a degree impossible in the past regarding a particular type of traumatized foot and in which the sole assembly may be effected as a unitary mid-sole with a lift wedge undersole, or a separate wedge shaped undersole fixed to the bottom of the post-operative shoe of the '767 patent as an attachment and by way of a suitable adhesive. The result is to create a post-operative shoe particularly useful after forefoot surgery, trauma to the forefoot, for the healing of plantar ulcerations or other lesions or to facilitate general medical treatment of the forefoot.

Figure 4:
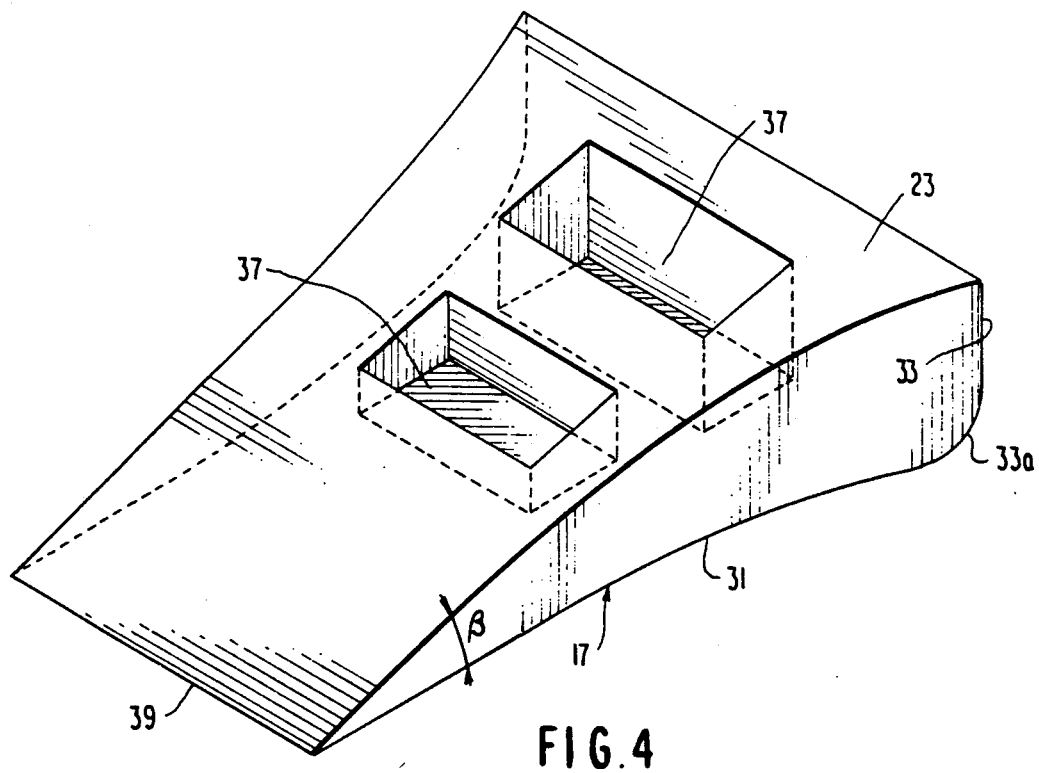
FIG. 4 is a perspective view of the lift wedge undersole of the shoe of FIG. 1.

FIG. 4 shows in a perspective view the lift wedge undersole 17, which is provided with a flat upper inclined surface 23 at an acute angle $\beta$ to a flat bottom surface 31, and has a flat front surface 33 which is at an acute angle to the upper surface 23 and at right angles with the bottom surface 31. Undersole 17 has a rounded edge 33a on the front surface 33 adjacent the bottom surface 31 so as to permit a slight rocking or rotation about the rounded edge 33a during patient ambulation. Preferably, one or more recesses 37 are formed within the lift wedge undersole 17, which element may be of molded rubber or other elastomer, the recesses 37 extending downwardly from the upper surface 23 towards the lower surface but terminating short thereof. The presence of the recesses or holes 37 does not adversely affect the ability of the lift wedge to maintain the bottom of the foot in vertically forwardly raised position, thus taking the weight off of the toes and forefoot of the patient. Further, the complete foot is supported by the soft insole 24 particularly the toes which protrude outwardly of the open end 51 of upper 12, but inwardly of the edge of insole 24, thus protecting the patient's exposed forefoot from side and front impact.

The shoe is thus designed to be used for any condition where it is desirable to remove the weight from the forefoot. By applying a layer of adhesive 25 to the upper surface 23 of the undersole 17, that block-like elastomer may be fixedly mounted to the bottom surface 21 of the mid-sole 16 to complete the shoe structure of FIG. 1 forward of an oblique cut-out 15 adjacent the heel 27 of the shoe 10. In that respect, cut-out 15 occurs in the vicinity of the heel 27 at an obtuse angle a to bottom surface 21a of the mid-sole over a short longitudinal distance 71 which is not in excess of 20% of the overall length 72 of sole assembly 14.

Further, the tapered lift wedge undersole 17 has a rear edge 39 which is flush to the bottom surface 21 of mid-sole 16 at the termination point 39 of cut-out 15 created by the upwardly and rearwardly oblique bottom surface portion 21a. From point 39 to tip 29 of the sole assembly 14, the bottom surface 21 is straight, giving a forwardly directed wedge contour to the mid-sole 16 in the direction of the toe 29 of the shoe.

Typical dimensions for the sole assembly 14 or its counterpart, a unitary one-piece sole, are as follows. The upper surface 18 of the mid-sole 16 is 24 cm in length for an extra small size post-operative shoe. The sole assembly 14 has a rear end surface 41 at heel 27 which extends downwardly at a near right angle to the upper surface 18 of mid-sole 16. The surface 41 intersects upwardly and rearwardly inclined bottom surface portion 21a of the mid-sole 16. The overall length of the mid-sole 16 and the lift wedge undersole 17 adhesively fixed thereto, or integral therewith, is 14.4 cm for the example given. The near vertical front surface 33 of the lift wedge undersole 17 sole assembly 14, FIG. 2, is at a point approximately 3/5 of the overall length of the sole assembly 14, from vertical heel surface 41 of mid-sole 16 towards toe vertical surface 43 of that mid-sole. The vertical height of near vertical front surface 33 of the lift wedge undersole 17 is 2.5 cm. The height of the near vertical surface 43 at toe 29 is 0.6 cm in the example given.

The lift wedge undersole 17 is adhesively connected to the mid-sole bottom surface 21 by the use of a hot or cold adhesive.

As may be appreciated, the shoe 10 is designed to be used for any condition where it is desirable to remove weight from the forefoot. The sole assembly 14, unlike the IPOS ® shoe, stops at the mid-metatarsal of the foot, leaving the affected forefoot area totally unprotected and making it uncomfortable to walk due to the pressure where the shoe ends under the mid-foot. No such action occurs in use of the improved post-operative shoe 10 of this invention. The mid-sole 16 continues uninterrupted from heel 27 to toe 29 as a decreasing thickness support for the forefoot from the mid-metatarsal forwardly, thus providing ample protection for the forefoot about and beyond the toes of the wearer, and full support for the forefoot for the duration of the healing process.

The sole assembly 14 of the shoe 10 is provided with a unitary or integral wedge undersole 17, which is preferably incorporated into the structure of the sole assembly 14. Alternatively, such undersole 17 may be sold separately as an attachable component to an existing post-operative shoe such as that shown in my U.S. Pat. No. 4,677,767. The wedge undersole extends down approximately 60% of the sole to terminate just proximate to the metatarsal heads, and the height of the wedge undersole is determined by the total length of the shoe.

On larger size shoes 10 the wedge undersole 17 is slightly higher than that of the smaller size as depicted in FIG. 1, to allow clearance of the longer toe portion of the shoe. The post-operative shoe 10 is believed to be the only surgical shoe of its kind to offer a combination of forefoot elevation and complete protection of the forefoot during the healing process for medical and surgical procedures.

It will be understood that while a preferred embodiment of the invention has been shown and described, particularly with respect to a modification of the surgical shoe as shown in my earlier U.S. Pat. No. 4,677,767, changes and additions may be made therein and thereto without departing from the spirit of the invention. Reference should, accordingly, be had to the appended claims in determining the scope of the invention.

What is claimed is:

1. In a post-operative shoe for use in elevating and supporting a post-operative or otherwise traumatized patient's foot comprising:
   an upper assembly secured to a sole assembly,
   said upper assembly adapted to surround the heel, sides and dorsal portions of the foot,
   said upper assembly having an open toe region,
   a heel region extending upwardly from the sole assembly,
   a forward portion divided into left and right flaps adapted to cover the dorsal region of the foot, and
   strap means interconnecting outer face portions of said left and right flaps,
   said sole assembly comprising an inner sole conforming generally to the plantar aspect of the foot, and a mid-sole of an impact-absorbing material having flat top and bottom surfaces and having a thickness which varies over the length of the shoe with its greatest thickness at the heel and tapering in the direction of the open toe region, the improvement comprising:
   a wedge undersole of triangular shape configuration, as viewed from a side thereof, having at least a flat bottom surface and being integrated to said mid-sole at the bottom thereof and in proximity to the heel of the shoe and being of a thickness such that the top surface of the mid-sole extends obliquely upwardly in the direction of the open toe region of the shoe, and wherein the wedge undersole terminates at an end remote from the shoe heel proximate to the metatarsal heads of the foot thereby transmitting pressure to the metatarsals just rearwardly of the M-P joint after forefoot surgery such as hammertoe procedures, mid-tarsal amputation, hallux valgus procedures, where lesions of any type are present on the forefoot or toes, and where ischemic changes including gangrene are present and involve the toes or forefoot; such that the weight and pressure of weight bearing on the forefoot is fully relieved while the portion of the mid-sole from the termination of the wedge undersole proximate to said metatarsal heads acts to fully support the forefoot at said upwardly oblique angle and to protect the forefoot from direct impact at both sides and at the front thereof.

2. The post-operative shoe as claimed in claim 1, wherein said wedge undersole is a separate element from said id-sole and has a flat top surface fixedly attached to the flat bottom surface of the mid-sole.

3. The post-operative shoe as claimed in claim 2, wherein an adhesive layer interposed between the top surface of the wedge undersole and the bottom surface of the mid-sole and adhesively fixes the wedge undersole to said mid-sole.

4. The post-operative shoe as claimed in claim 1, wherein said wedge undersole is integrally molded with said mid-sole.

5. The post-operative shoe as claimed in claim 1, wherein said mid-sole has a flat, rearwardly upward oblique bottom surface portion thereof extending from said rear edge of said tapered wedge undersole to said heel to form with the bottom surface of said wedge undersole a rear rocking point for said post-operative shoe during ambulation of the patient.

6. The post-operative shoe as claimed in claim 1, wherein said wedge undersole has s front surface at said metatarsal heads which extends vertically upwardly at a near right angle with the flat bottom surface of said wedge undersole, thereby forming a front rocking point for said post-operative shoe for facilitating ambulation of the patient.

7. The post-operative shoe as claimed in claim 1, wherein at least, in the vicinity of said front surface, said wedge undersole is of solid to rigidify the sole assembly in the area of the front rocking point to facilitate rocking of the post-operative shoe about the front rocking point during ambulation of the patient.

8. In a post-operative shoe for use in elevating and supporting a post-operative or otherwise traumatized patient's foot comprising:
    an upper assembly secured to a sole assembly, said upper assembly adapted to surround the heel, sides and dorsal portions of the foot and having an open toe region, a heel region upwardly from the sole assembly and a forward portion leading from the heel region to the open toe region and means for enveloping the dorsal portion of the foot, said sole assembly comprising: at least a mid-sole of an impact-absorbing material having a flat top surface, the improvement comprising:
    a wedge undersole of triangular shape configuration as viewed from a side thereof integrated to the mid-sole at the bottom thereof in proximity to the heel of the shoe and tapering from a front surface thereof to a rear edge and being of a thickness such that the top surface of the mid-sole extends obliquely upwardly in the direction of the open toe region of the shoe, and wherein the wedge undersole terminates at an end remote from the shoe heel region with said front surface proximate to the metatarsal heads of the foot thereby transmitting pressure to the metatarsals just rearwardly of the M-P joint such that the pressure of bearing weight on the forefoot is fully relieved after forefoot surgery as following hammertoe procedures; after mid-tarsal amputation, after hallux valgus procedures; where diabetic ulcerations are present beneath the M-P joints or toes; where lesions are present on the forefoot or toes; and where ischemic changes including gangrene are present and involve the toes or forefoot, while the portion of the mid-sole extending from the termination of the wedge undersole proximate to said metatarsal heads in the direction of the open toe region act to fully support said forefoot at said upwardly oblique angle and protects the forefoot from direct impact along both sides and at the front of said mid-sole, beyond said open toe region, and wherein said wedge undersole includes a flat bottom surface which is generally horizontal and wherein the top surface of the mid-sole extends at said obliquely upward angle in the direction of the open toe region of the shoe.

* * * * *